(12) United States Patent  
Brents et al.

(10) Patent No.: US 8,303,905 B2
(45) Date of Patent: Nov. 6, 2012

(54) GERM ELIMINATOR SYSTEM

(76) Inventors: Rebecca Brents, Kingsland, TX (US); Steve Brents, Kingsland, TX (US)

( * ) Notice: Subject to any disclaimer, the term of this patent is extended or adjusted under 35 U.S.C. 154(b) by 175 days.

(21) Appl. No.: 12/780,897

(22) Filed: May 15, 2010

(65) Prior Publication Data

US 2010/0290958 A1 Nov. 18, 2010

Related U.S. Application Data

(60) Provisional application No. 61/178,735, filed on May 15, 2009.

(51) Int. Cl.
*A61L 2/00* (2006.01)
*A61L 9/00* (2006.01)
*A61L 2/18* (2006.01)

(52) U.S. Cl. ........... 422/292; 422/28; 422/294; 422/295

(58) Field of Classification Search .................. 422/292, 422/294, 295, 28; 137/624.11, 624.14; 134/88, 134/95.3, 103.2; 62/390
See application file for complete search history.

(56) References Cited

U.S. PATENT DOCUMENTS

| | | | | |
|---|---|---|---|---|
| 3,096,775 A | * | 7/1963 | Clarke et al. | 134/123 |
| 3,289,238 A | * | 12/1966 | Sorenson et al. | 15/306.1 |
| 3,444,867 A | * | 5/1969 | Thornton | 134/123 |
| 3,653,444 A | * | 4/1972 | Livingston | 169/5 |
| 3,736,948 A | * | 6/1973 | Crosswhite | 134/95.2 |
| 3,797,744 A | | 3/1974 | Smith | |
| 3,819,329 A | | 6/1974 | Kaestner et al. | |
| 3,943,960 A | | 3/1976 | Syrenne | |
| 4,914,339 A | * | 4/1990 | Hayman et al. | 312/115 |
| 5,213,117 A | * | 5/1993 | Yamamoto | 134/58 R |
| 5,263,504 A | * | 11/1993 | Bailey et al. | 134/176 |
| 5,487,346 A | * | 1/1996 | Taylor | 111/127 |
| 5,601,100 A | * | 2/1997 | Kawakami et al. | 134/56 R |
| 6,427,707 B1 | * | 8/2002 | Morris | 134/72 |
| 7,290,457 B2 | * | 11/2007 | Kudo et al. | 73/865.9 |
| 2004/0031507 A1 | * | 2/2004 | Ross et al. | 134/123 |
| 2005/0112022 A1 | | 5/2005 | Morgan | |
| 2009/0071062 A1 | | 3/2009 | Hedman | |
| 2010/0065287 A1 | * | 3/2010 | Burkhart et al. | 169/17 |

* cited by examiner

*Primary Examiner* — Regina M. Yoo
(74) *Attorney, Agent, or Firm* — Thien Tran, Esq; Access Patent Group, LLC (57) ABSTRACT

A germ eliminator system is for disinfecting an enclosure which includes a green disinfectant liquid. A mechanism is for distributing the disinfectant liquid in a timely and sequentially manner throughout the enclosure, to kill germs, bacteria, viruses and other microorganisms within the enclosure, thereby the enclosure will become safe for people to use when entering the enclosure such as building, hotel, school, bus, train, or ship. The germ eliminator system can be stationary or mobile on a service cart.

10 Claims, 11 Drawing Sheets

GERM ELIMINATOR SYSTEM

CROSS-REFERENCE TO RELATED APPLICATION

This application claims the benefit of Provisional Patent Application No. 61/178,735, filed on May 15, 2009, in the United States Patent & Trademark Office, the disclosure of which is incorporated herein by reference.

BACKGROUND OF THE INVENTION

1. Field of the Invention

The present invention relates to a disinfectant device, and more particularly, a germ eliminator system.

2. Description of the Prior Art

Many people may fall ill after being exposed to germs and bacteria in crowded areas. Offices, schools and similar places can easily breed viruses that can make a person sick. Individuals may dread becoming ill because of the physical consequences, but may also not want to miss work or school. Caregivers must often take days off of work in order to care for themselves or a sick child. Doctor visits and prescriptions can also be costly. Confined spaces, such as public transportation vehicles, can easily expose a patron to assorted germs and viruses. Having a simple and effective way to sanitize a specific area when it is empty may assist individuals in staying germ-free and healthy.

Numerous innovations for chemical dispensers have been provided in the prior art that will be described. Even though these innovations may be suitable for the specific individual purposes to which they address, however, they differ from the present invention.

A FIRST EXAMPLE, U.S. Patent Office Document No. 3,797,744, issued on Mar. 19, 1974, to Smith teaches a wheeled frame, supporting a series of chemical tanks connected to the manifold, which includes a high pressure pump for a high pressure, low volume, or low pressure, high volume, cleaning and disinfecting capability. It has a metered and controlled selected chemical injection produced by a high pressure proportioning pump downstream of the high pressure water pump which pumps chemicals from the chemical tanks into the pressurized fluid stream. An additional capability is a metered and controlled oil injection into a high pressure air stream, which also has a drying capacity when oil is not metered into the system. The unit requires connections for electrical, power, and air which are locally available in the areas to be cleaned. Cleaning and disinfecting may be readily achieved by use of a detergent foam, then a high or low pressure chemical wash and followed by a sterilizing solution, and then by a clear-water low pressure rinse, all of which is followed by an oiling of clean equipment. Quick disconnect service terminals provide fast and easy set-up and take-down of the unit.

A SECOND EXAMPLE, U.S. Patent Office Document No. 3,819,329, issued on Jun. 25, 1974, to Kaestner et al. teaches a spray sanitizing system for creating a continuous supply of sanitizing liquid with a hand operable wand having a liquid discharge nozzle and a portable central generator unit which includes an electrolytic cell for instantaneously generating a relatively low pH bactericidal solution containing nascent chlorine substantially entirely in the form of hypochlorous acid.

A THIRD EXAMPLE, U.S. Patent Office Document No. 3,943,960, Issued on Mar. 16, 1976, to Syrenne teaches dispensers for chemicals usually have ball check valves and other moving parts which often corrode due to the action of the chemical. Other types may eliminate the moving parts, but have to be re-charged each time they are used. This device consists of a container having a water inlet and a water outlet at the under end. A U-shaped tube depends within the container and is secured to the inlet and outlet means is provided with a plurality of small holes to allow some of the water to enter a container. An outlet branch is secured within the container, to the outlet means and water is picked up from the container by the outlet branch and joins the mainstream of water passing through the U-shaped tube. Chemical in a fabric bag is placed in the container and dissolves in the water in the container and is picked by the outlet tube. When the water is shut off, the container may drain by siphoning action until the outlet branch is reached by the water level which breaks the siphon action so that some water always remains in the container covering the bag in order to dissolve the chemical contained therein.

A FOURTH EXAMPLE, U.S. Patent Office Publication No. 20050112022, Published on May 26, 2005, to Morgan teaches an aerosol canister containing sanitizing liquid and propellant to sanitize exposed surfaces in a room in a short period of time. The canister is placed in a closed room and its dispensing valve is actuated to dispense the sanitizing liquid in an aerosol mist of droplets which expand to fill the room in mere minutes. The canister can include a weighted rounded base to enable the canister to be tossed into the room and assume an upright dispensing position. The base can be filled with weighting material just before use. One embodiment can be rolled into the room.

A FIFTH EXAMPLE, U.S. Patent Office Publication No. 20090071062, published on Mar. 19, 2009, to Hedman teaches a process for removing or treating harmful biological and chemical substances from an enclosure, such as a building or vehicle by using heated air. The method of the present invention is non-toxic and can be performed in a relatively short amount of time while effectively killing and removing a large proportion of dead organisms and substantially reducing volatile organic compounds.

It is apparent now that numerous innovations for chemical dispensers have been provided in the prior art that are adequate for various purposes. Furthermore, even though these innovations may be suitable for the specific individual purposes to which they address, accordingly, they would not be suitable for the purposes of the present invention as heretofore described.

SUMMARY OF THE INVENTION

AN OBJECT of the present invention is to provide a germ eliminator system that avoids the disadvantages of the prior art.

ANOTHER OBJECT of the present invention is to provide a germ eliminator system that is simple and inexpensive to manufacture.

STILL ANOTHER OBJECT of the present invention is to provide a germ eliminator system that is simple to use.

STILL ANOTHER OBJECT of the present invention is to provide a germ eliminator system that is used with green non-toxic products and is environmentally safe.

BRIEFLY STATED, STILL YET ANOTHER OBJECT of the present invention is to provide a germ eliminator system for disinfecting an enclosure which comprises a green disinfectant liquid. A mechanism is for distributing the green disinfectant liquid throughout the enclosure, to kill germs, bacteria, viruses and other microorganisms within the enclosure, thereby the enclosure will become safe for people to use when they enter the enclosure.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawings are briefly described as follows.

REFERENCE NUMERALS UTILIZED IN THE DRAWING 110 germ eliminator system
112 enclosure
114 disinfectant liquid of system 110
116 distributing mechanism of system 110
118 green disinfecting non-toxic chemical for disinfectant liquid 114
120 holding tank of mechanism 116
122 first shut-off valve of mechanism 116
124 bottom exit port of holding tank 120
126 first drain valve of mechanism 116
128 check valve of mechanism 116
130 electric pump of mechanism 116
132 inlet port of electric pump 130
134 second shut-off valve of mechanism 116
136 outlet port of electric pump 130
138 first pressure gauge of mechanism 116
140 pressure relief valve of mechanism 116
142 first excess return pipe of mechanism 116
144 first top inlet port of holding tank 120
146 second pressure gauge of mechanism 116
148 first solenoid valve of mechanism 116
150 second drain valve of mechanism 116
152 elongated main pipe of mechanism 116
154 wall of enclosure 112
156 ceiling of enclosure 112
158 misting nozzle housing of mechanism 116
159 an optional mobile service cart for the germ eliminator system
160 third drain valve of mechanism 116
162 second solenoid valve of mechanism 116
164 second excess return pipe of mechanism 116
166 second top inlet port of holding tank 120
170 top air vent port in holding tank 120
172 electric timer of mechanism 116
174 starter box of mechanism 116
176 stainless steel check valve body of misting nozzle housing 158
178 first rubber O-ring of misting nozzle housing 158
180 second rubber O-ring of misting nozzle housing 158
182 stainless steel check plunger of misting nozzle housing 158
184 stainless steel compression spring of misting nozzle housing 158
186 stainless steel nozzle head of misting nozzle housing 158
188 stainless steel misting nozzle in nozzle head 186

DETAILED DESCRIPTION OF THE PREFERRED EMBODIMENT

Referring now to the figures, in which like numerals indicate like parts, and particularly to FIGS. 1 through 11, and as such, will be discussed with reference thereto.

The present invention is a germ eliminator system 110 for disinfecting an enclosure 112 which comprises a green disinfectant liquid 114. A mechanism 116 is for distributing the green disinfectant liquid 114 throughout the enclosure 112, to kill germs, bacteria, viruses and other microorganisms within the enclosure 112, thereby the enclosure 112 will become safe for people to use when they enter the enclosure 112. The green disinfectant liquid 114 comprises a green disinfecting non-toxic chemical 118 that will neutralize the harmful effects of the germs, bacteria, viruses and other microorganisms within the enclosure 112. The germ eliminator system can be stationary or mobile on a service cart (FIG. 1B).

Figure 1A:
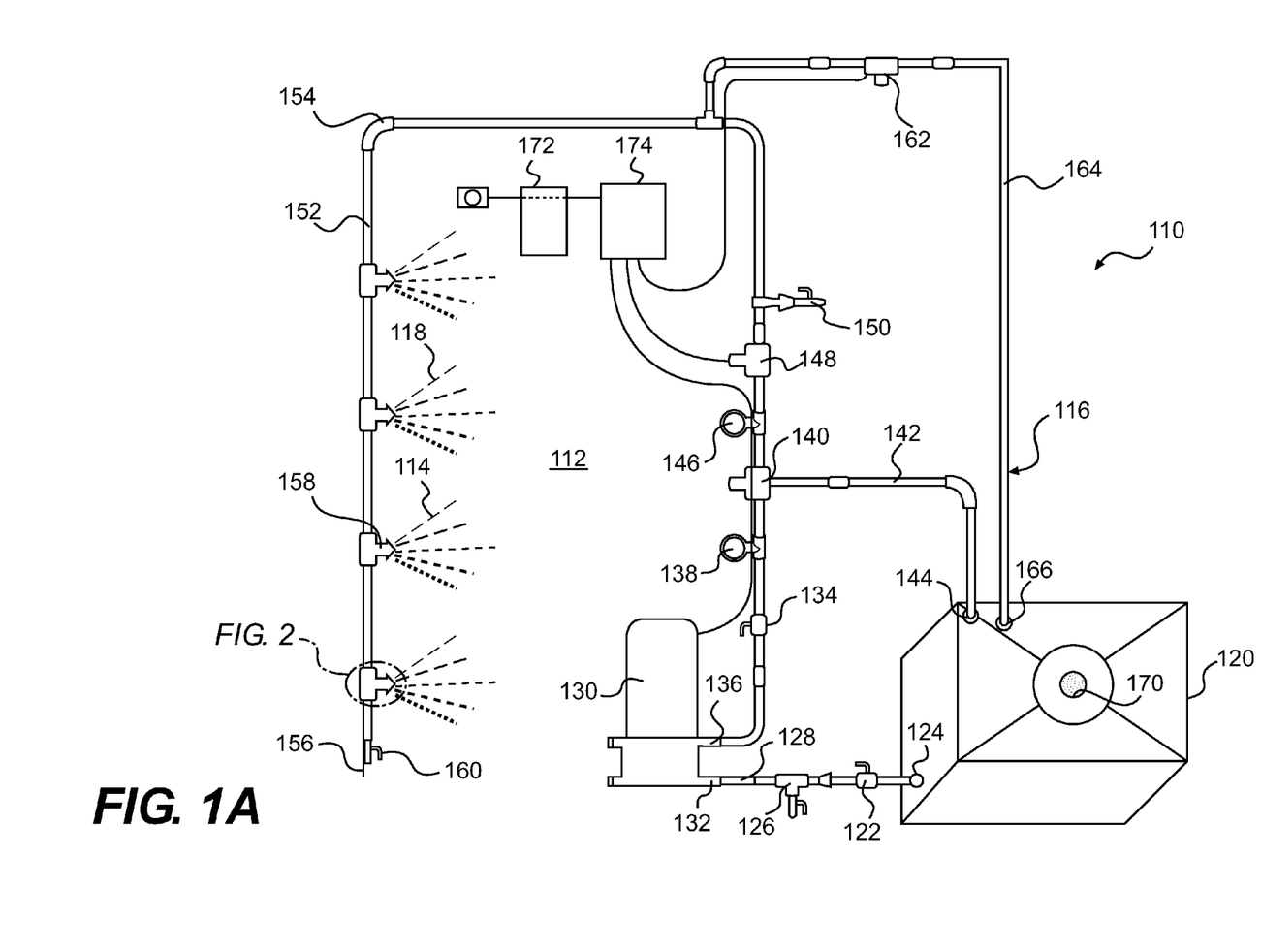
FIG. 1 is a diagrammatic view showing the various components of the present invention.
Figure 1B:
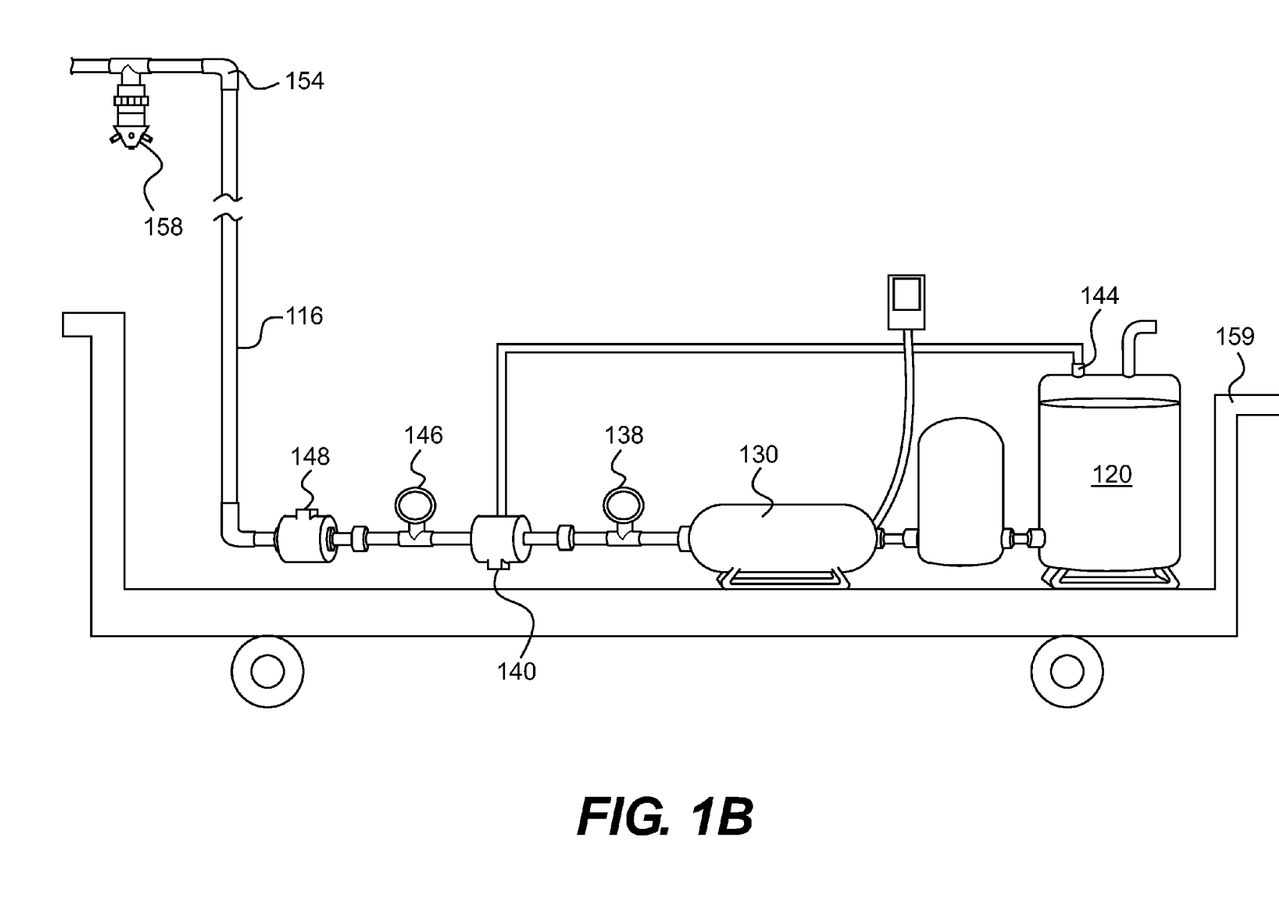

The distributing pipe mechanism 116, as best seen in FIG. 1A, comprises a holding tank 120 to receive the green disinfectant liquid 114 therein. The first shut-off valve 122 is fluidly connected to a bottom exit port 124 of the holding tank 120. A first drain valve 126 is fluidly connected to the first shut-off valve 122.

A check valve 128 is fluidly connected to the first drain valve 126. An electric pump 130 has an inlet port 132 fluidly connected to the check valve 128. A second shut-off valve 134 is fluidly connected to an outlet port 136 of the electric pump 130. A first pressure gauge 138 is fluidly connected to the second shut-off valve 134.

A pressure relief valve 140 is fluidly connected to the first pressure gauge 138. A first excess return pipe 142 is fluidly connected between the pressure relief valve 140 and a first top inlet port 144 of the holding tank 120. A second pressure gauge 146 is fluidly connected to the pressure relief valve 140. A normally closed first solenoid valve 148 is fluidly connected to the second pressure gauge 146. A second drain valve 150 is fluidly connected to the first solenoid valve 148. An elongated main pipe 152 is fluidly connected to the second drain valve 150. The elongated main pipe 152 extends up from a wall 154 to a ceiling 156 of the enclosure 112. A plurality of misting nozzle housings 158 are spaced apart and fluidly connected to the elongated main pipe 152 at the ceiling 156 of the enclosure 112. The misting nozzle housings 158 will direct the green disinfectant liquid 114 into the enclosure 112.

A third drain valve 160 is fluidly connected to a distal end of the elongated main pipe 152. A second normally closed solenoid valve 162 is fluidly connected to the elongated main pipe 152 between the second drain valve 150 and the misting nozzle housings 158. A second excess return pipe 164 is fluidly connected between the second solenoid valve 162 and a second top inlet port 166 of the holding tank 120. A top air vent port 170 is in the holding tank 120. An optional service cart 159 can be used for the germ eliminator system 110.

Figures 2, 3:
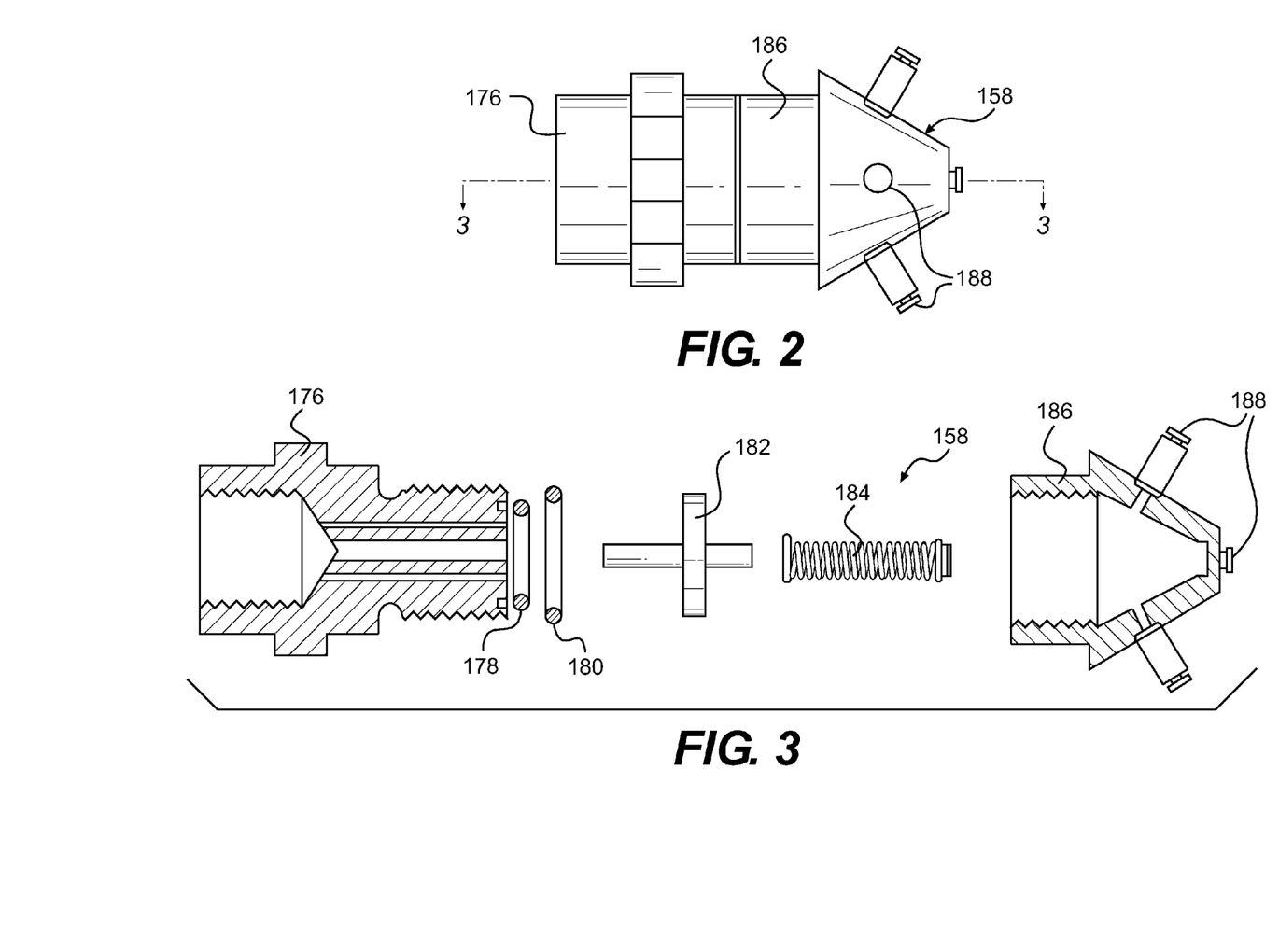
FIG. 2 is an enlarged elevational view of one misting nozzle housing located in the dotted area and indicated by arrow 2 in FIG. 1.
FIG. 3 is an enlarged exploded view partially in cross section taken along line 3-3 in FIG. 2 showing the various components of the misting nozzle housing.

An electric timer 172 is set at different time intervals. A starter box 174 electrically connected to and controlled by the electric timer 172. The starter box 174 is electrically connected to the electric pump 130, the first solenoid valve 148 and the second solenoid valve 162. When the timer 172 goes off it will activate the starter box 174 which starts the electric pump 130 and opens the first solenoid valve 148 and the second solenoid valve 162. The second solenoid valve 162 opens in sequential (or sequential time or sequence) from timer 172 after solenoid valve 148 ($1^{st}$ valve) closes. Each misting nozzle housing 158, as best seen in FIGS. 2 and 3, comprises a stainless steel check valve body 176, two rubber O-rings 178 and 180, a stainless steel check plunger 182, a stainless steel compression spring 184 and a stainless steel nozzle head 186 having a plurality of stainless steel misting nozzles 188 thereabout.

Figure 4:
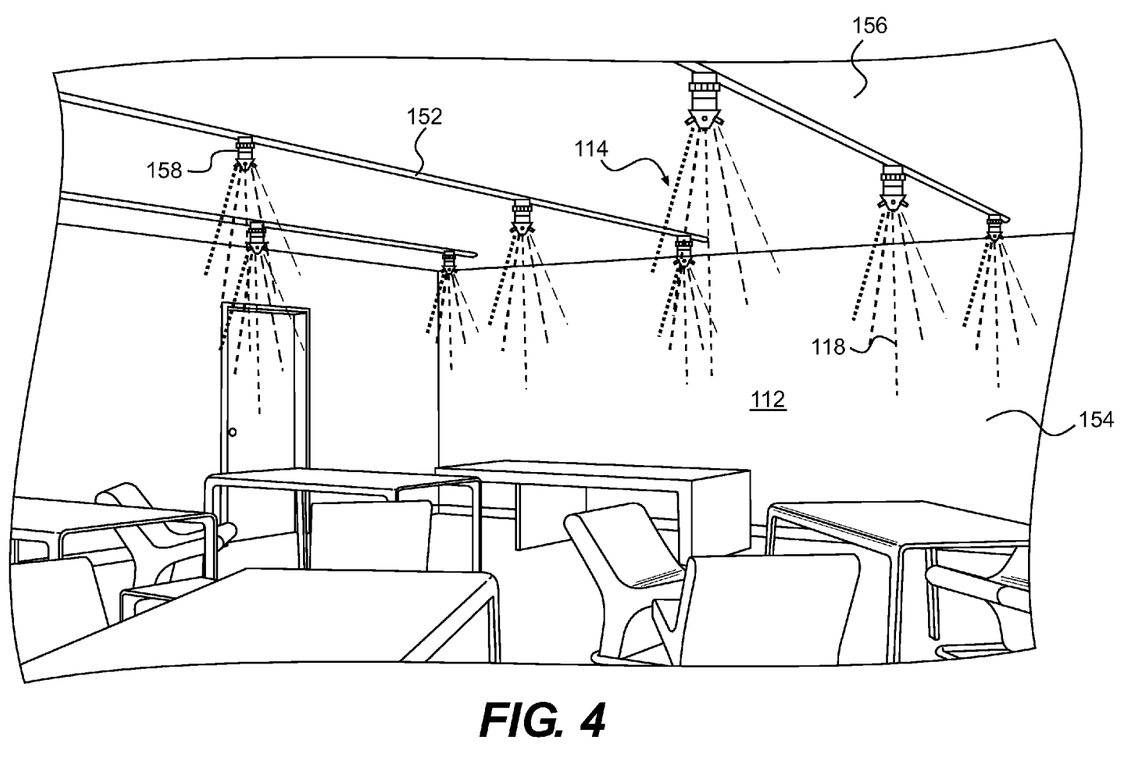
FIG. 4 is a perspective view showing the present invention being used in a stationary enclosure, such as a classroom.
Figure 5:
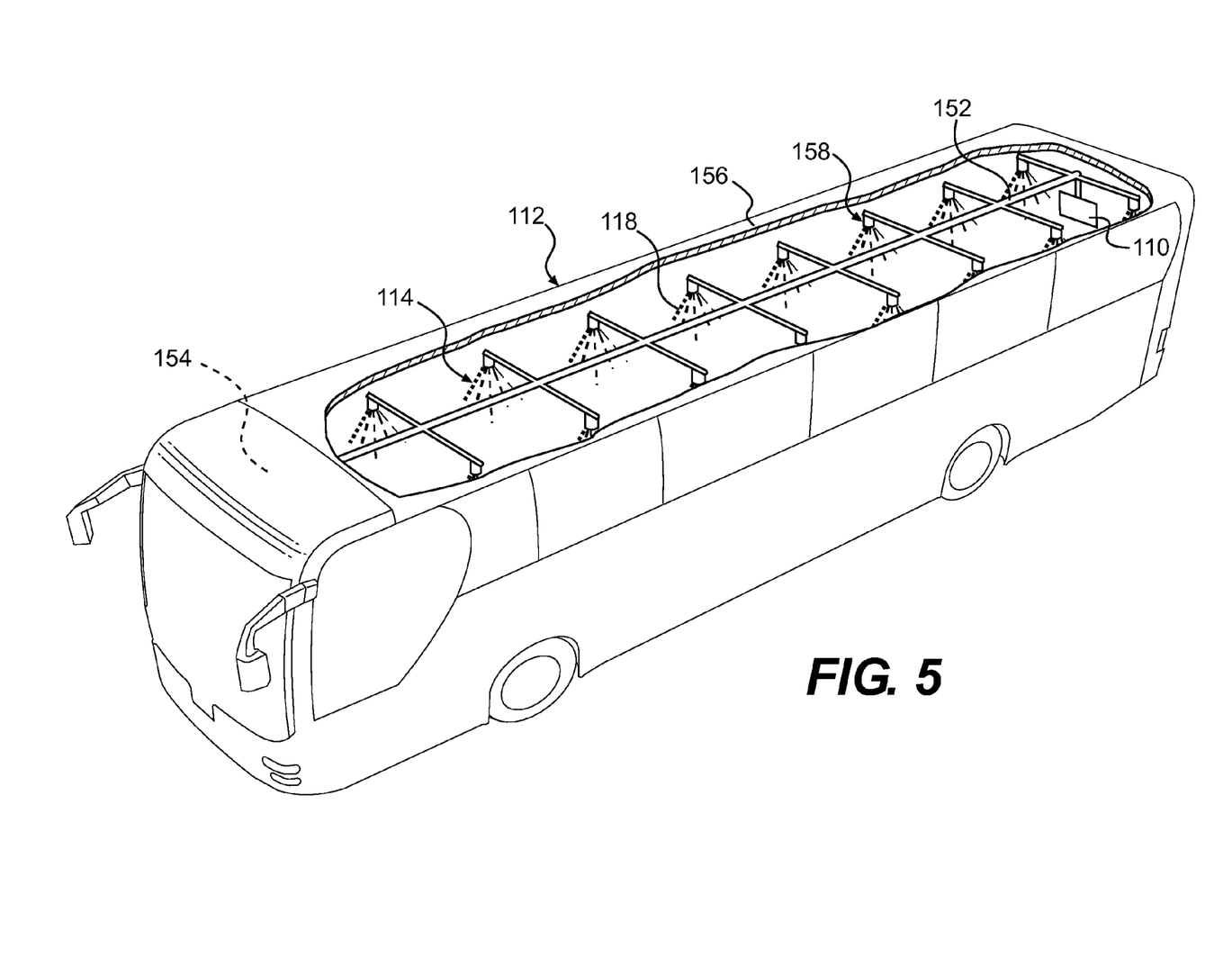
FIG. 5 is a perspective view, with parts broken away, showing the present invention being used in a mobile enclosure, such as a bus with a stationary germ eliminator system.
Figure 6:
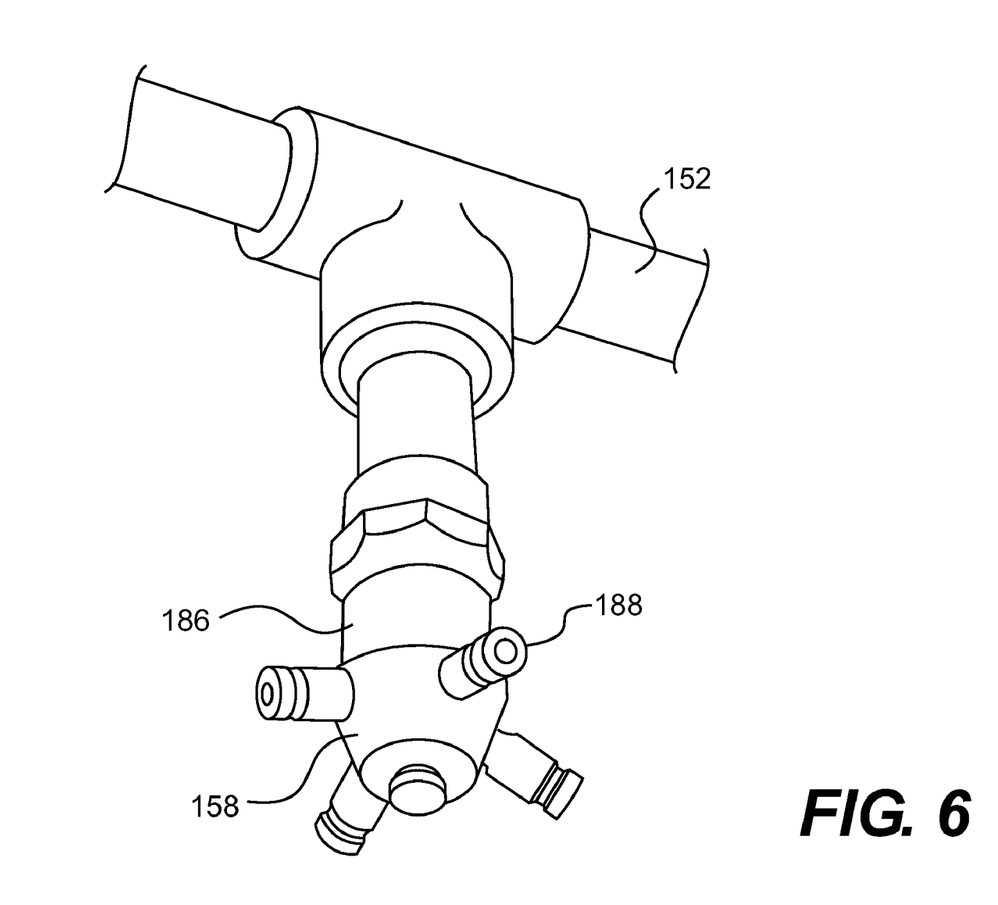
FIG. 6 is view of the mist nozzle.
Figure 7:
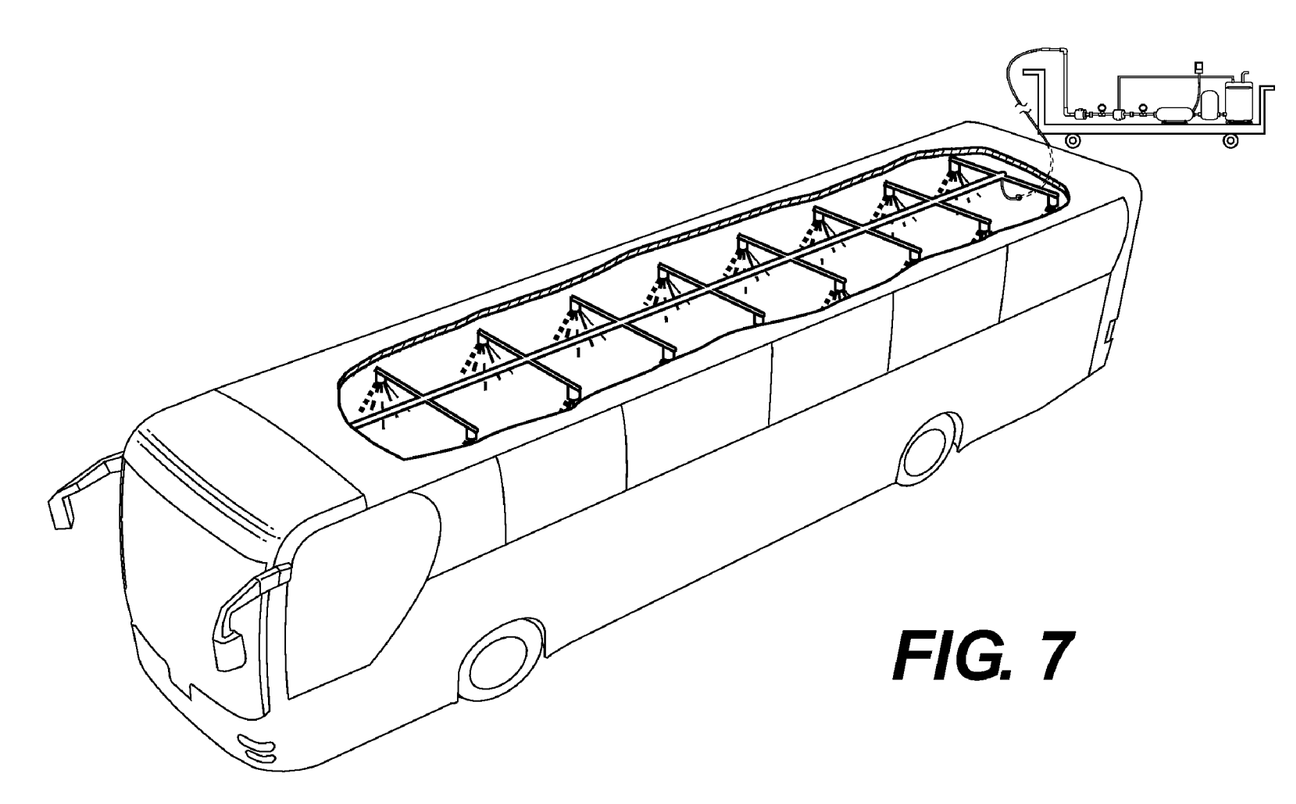
FIG. 7 is a view of a bus with a mobile germ eliminator system.
Figure 8:
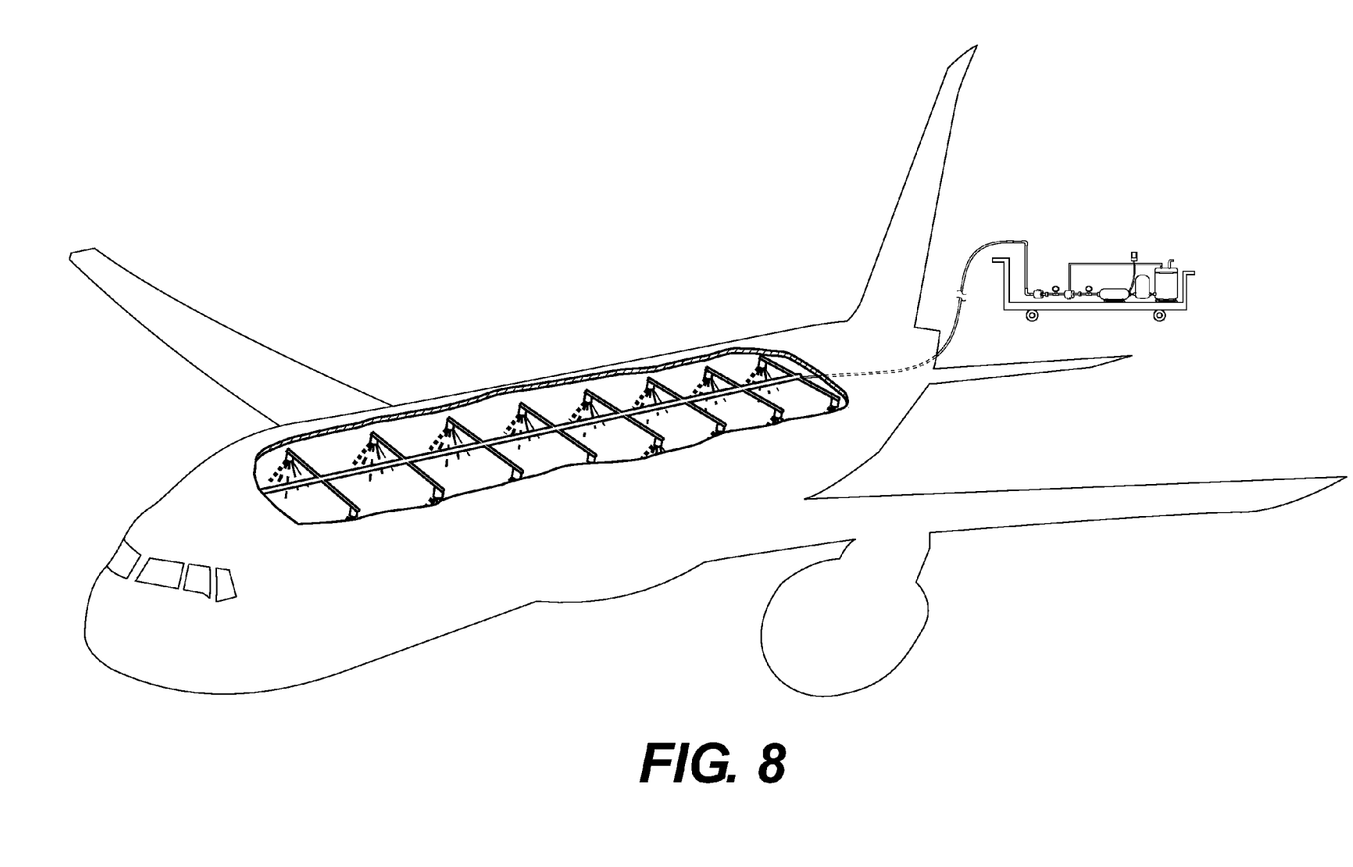
FIG. 8 is a view of an airplane with a mobile germ eliminator system.
Figure 9:
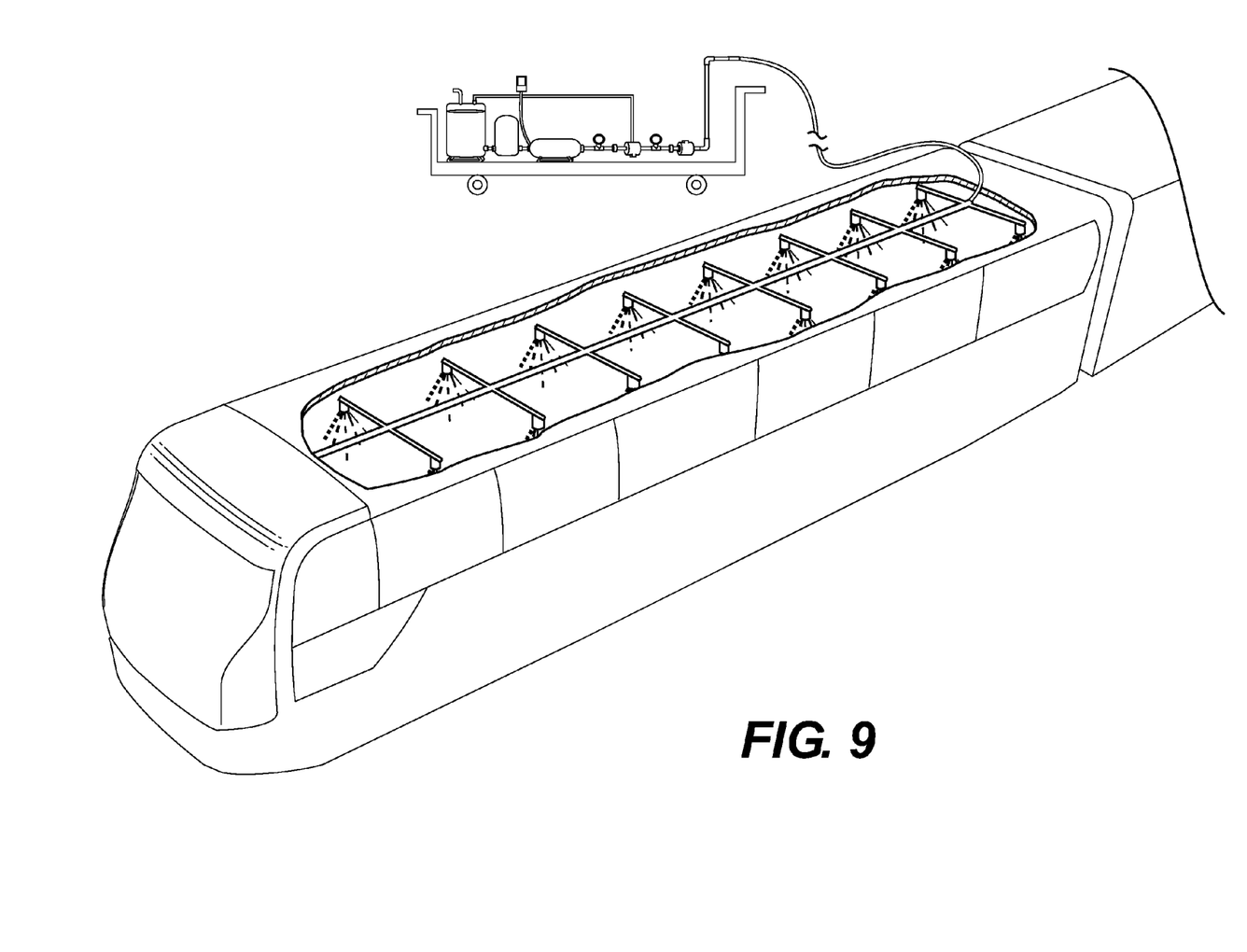
FIG. 9 is a view of a train with a mobile germ eliminator system.
Figure 10:
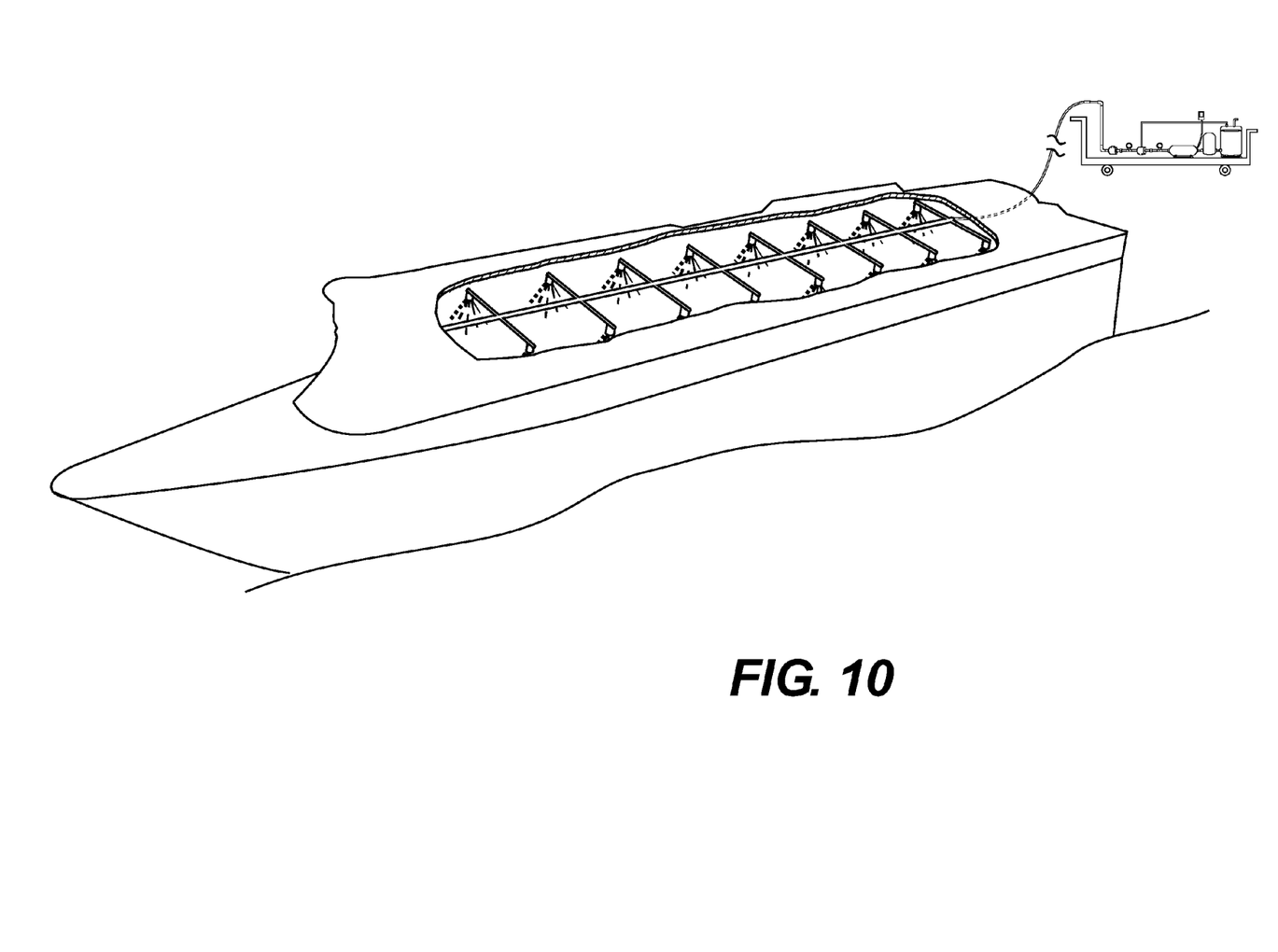
FIG. 10 is a view of a ship with a mobile germ eliminator system.

The enclosure 112, as seen in FIG. 4 is stationary and can be selected from the group consisting of a building, a hotel, a public school, a church, a hospital, a laboratory and any other stationary structure. The enclosure 112, as seen in FIG. 5, is mobile and can be selected from the group consisting of a bus, an airplane, a ship, a train and any other mobile structure.

The germ eliminator system 110 provides individuals with a simple way to rid various rooms of microorganisms so occupants may remain healthy. The present invention can assist individuals in removing bacteria and germs from rooms in a quick and efficient manner. The germ eliminator system 110 is ideal for use after hours in schools, clinics, medical offices, restaurants and any other building that may need to be regularly disinfected to reduce the number of viruses that may exist in the establishment.

Figure 11:
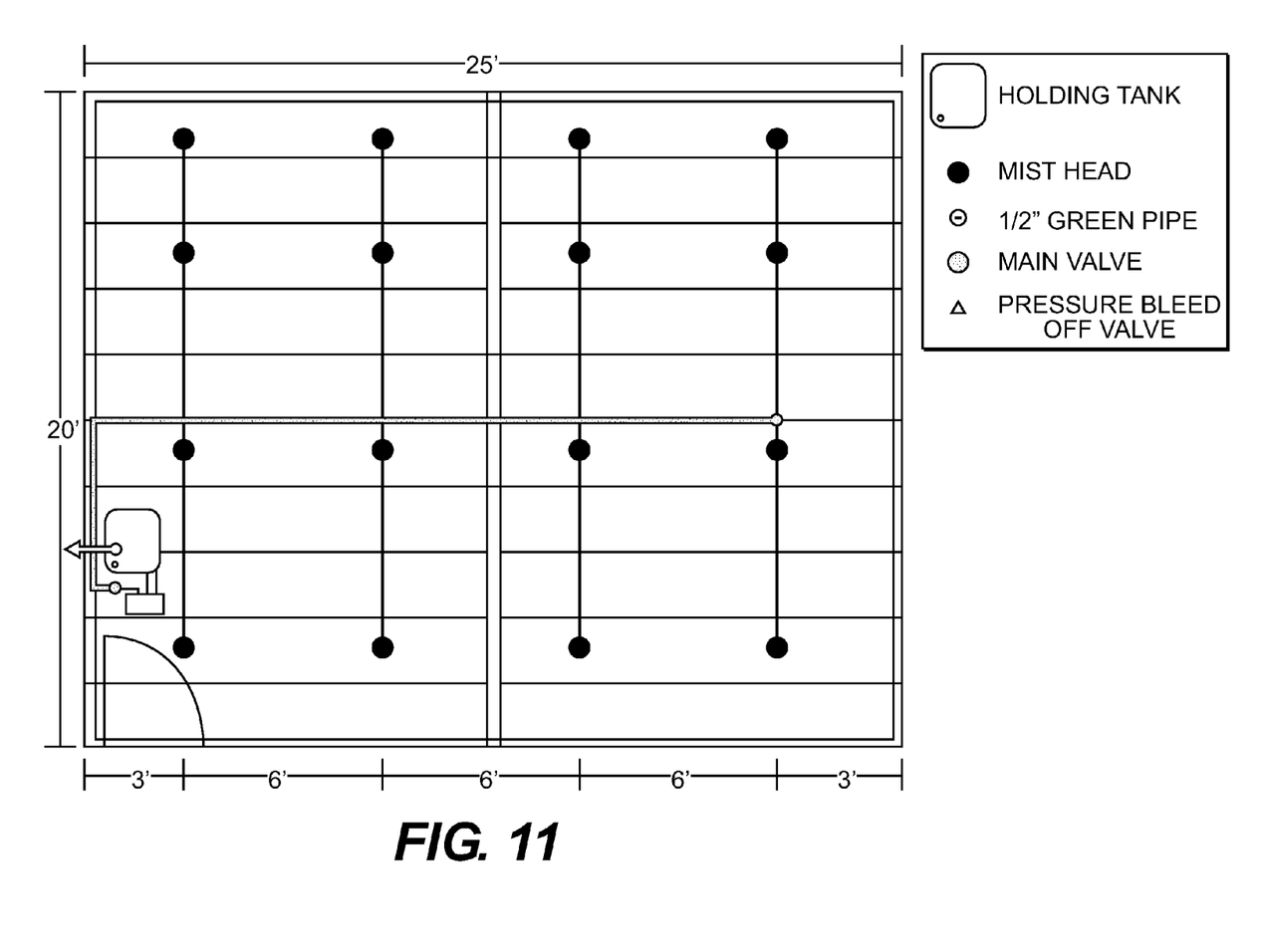
FIG. 11 is a view of a floor plan using with the germ eliminator system.

The germ eliminator system 110 is an arrangement of components that work together to efficiently disinfect an unoccupied room, train, vehicle, bus, airplane or ship. The present invention is equipped to rooms, buildings, buses, ships, airplanes and trains in the same way that an emergency sprinkler system is operated and installed. Instead of water, the misting nozzle housings 158 will spray the green disinfectant liquid 114 safely. The electric timer 172 is used to activate the starter box 174 at a time desired by the user. The time must be after the room or vehicle has been emptied of people. The various components of the germ eliminator system 110 that include the electric pump 130 and the holding tank 120 which work together in a predetermined manner to provide a misting spray may be kept in a separate room. The misting nozzle housings 158 are installed into the ceilings of rooms and transportation vehicles in predetermined locations. FIG. 11 shows a floor plan using with the germ eliminator system 110. The exact dimensions, materials used for construction and method of operation of the germ eliminator system 110 may vary upon manufacturing.

It will be understood that each of the elements described above, or two or more together, may also find a useful application in other types of constructions differing from the types described above.

While the invention has been illustrated and described as embodiments of a germ eliminator system, accordingly it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A germ eliminator system for sanitizing an enclosure which comprises:
   a) a disinfectant liquid in a holding tank being pumped to a distribution pipe system located on a top ceiling of the enclosure;
   b) an electric timer being set at different time intervals for a flow of said disinfectant liquid in said pipe system;
   c) a plurality of misting nozzles at the ends of the pipe system for distributing said disinfectant liquid throughout the enclosure in said time intervals set by the electric timer, to kill germs, bacteria, viruses and other microorganisms within the enclosure; and said distributing pipe system further comprises:
      1) a first shut-off valve fluidly connected to a bottom exit port of said holding tank;
      2) a first drain valve fluidly connected to said first shut-off valve;
      3) a check valve fluidly connected to said first drain valve;
      4) an electric pump having an inlet port fluidly connected to said check valve;
      5) a second shut-off valve fluidly connected to an outlet port of said electric pump;
      6) a first pressure gauge fluidly connected to said second shut-off valve;
      7) a pressure relief valve fluidly connected to said first pressure gauge;
      8) a first excess return pipe fluidly connected between said pressure relief valve and a first top inlet port of said holding tank;
      9) a second pressure gauge fluidly connected to said pressure relief valve;
      10) a normally closed first solenoid valve fluidly connected to said second pressure gauge;
      11) a second drain valve fluidly connected to said first solenoid valve;
      12) an elongated main pipe fluidly connected to said second drain valve, whereby said elongated main pipe extends up from a wall to a ceiling of the enclosure; and
      13) a plurality of misting nozzle housings, spaced apart and fluidly connected to said elongated main pipe at the ceiling of the enclosure, wherein said misting nozzle housings will direct said disinfectant liquid via said plurality of misting nozzles into the enclosure.

2. The germ eliminator system as recited in claim 1, wherein said disinfectant liquid comprises a green sanitizing non-toxic chemical that will neutralize the harmful effects of the germs, bacteria, viruses and other microorganisms within the enclosure.

3. The germ eliminator system as recited in claim 1, wherein said distribution pipe system further comprises:
   a) a third drain valve fluidly connected to a distal end of said elongated main pipe;
   b) a second normally closed solenoid valve fluidly connected to said elongated main pipe between said second drain valve and said misting nozzle housings; and c) a second excess return pipe fluidly connected between said second solenoid valve and a second top inlet port of said holding tank.

4. The germ eliminator system as recited in claim 3, wherein said distributing pipe system further comprises:
a) a top fill inlet pipe in said holding tank; and
b) a top air vent port in said holding tank.

5. The germ eliminator system as recited in claim 4, wherein said distributing pipe system further comprises:
a starter box electrically connected to and controlled by said electric timer, whereby said starter box is electrically connected to said electric pump, said first solenoid valve and said second solenoid valve, wherein when said timer goes off, the timer will activate said starter box which starts said electric pump and opens said first solenoid valve and said second solenoid valve.

6. The germ eliminator system as recited in claim 1, wherein each said misting nozzle comprises:
a) a stainless steel check valve body;
b) two rubber O-rings;
c) a stainless steel check plunger;
d) a stainless steel compression spring; and
e) a stainless steel nozzle head having a plurality of stainless steel misting nozzles thereabout.

7. The germ eliminator system as recited in claim 1, wherein the enclosure is stationary and is selected from the group consisting of a building, a hotel, a public school, a church, a hospital, a laboratory and any other stationary structure.

8. The germ eliminator system as recited in claim 1, wherein the enclosure is mobile and is selected from the group consisting of a bus, an airplane, a ship, a train and any other mobile structure.

9. The germ eliminator system as recited in claim 1, wherein the germ eliminator system can be mounted on a mobile service cart.

10. The germ eliminator system as recited in claim 1, wherein the germ eliminator system can be stationary.

* * * * *